(12) United States Patent
Russo et al.

(10) Patent No.: US 7,495,105 B2
(45) Date of Patent: Feb. 24, 2009

(54) NON-RACEMIC MIXTURES OF (S) AND (R) ENANTIOMERS OF N-(2,6-DIMETHYLPHENYL)-1-PROPYL-2-PIPERIDINOCARBOXAMIDE; RELATED PROCESSES AND PHARMACEUTICAL COMPOSITIONS

(75) Inventors: Valter Freiro Torres Russo, Sao Paulo (BR); Elisa Mannochio de Souza Russo, Sao Paulo (BR); Ogari de Castro Pacheco, Sao Paulo (BR)

(73) Assignee: Cristalia Produtos Quimicos Farmaceuticos Ltda., Itapira (BR)

( * ) Notice: Subject to any disclaimer, the term of this patent is extended or adjusted under 35 U.S.C. 154(b) by 0 days.

(21) Appl. No.: 10/491,924

(22) PCT Filed: Oct. 8, 2002

(86) PCT No.: PCT/BR02/00140
§ 371 (c)(1),
(2), (4) Date: Apr. 8, 2004

(87) PCT Pub. No.: WO03/053326
PCT Pub. Date: Jul. 3, 2003

(65) Prior Publication Data
US 2004/0210057 A1    Oct. 21, 2004

(30) Foreign Application Priority Data
Oct. 10, 2001    (BR) .................................. 0104491

(51) Int. Cl.
*C07D 211/22*    (2006.01)
*C07D 211/26*    (2006.01)
*A61K 31/4458*    (2006.01)

(52) U.S. Cl. ........................ 546/225; 514/330; 514/331

(58) Field of Classification Search ................. 546/225; 514/330, 331
See application file for complete search history.

(56) References Cited

U.S. PATENT DOCUMENTS 4,695,576 A    9/1987    af Ekenstam et al.
4,870,086 A    9/1989    Sandberg
(Continued)

OTHER PUBLICATIONS

Clinical pharmacology through the looking glass, Lennard M.S. 1991.*
(Continued)

*Primary Examiner*—Rita J Desai
(74) *Attorney, Agent, or Firm*—Birch, Stewart, Kolasch & Birch, LLP

(57) ABSTRACT

The present invention describes a method of separation of the enantiomers of N-(2,6-dimethylphenyl)-1-propyl-2-piperidinocarboxamide. Another object of the present invention refers to the enantiomeric manipulation of the enantiomers of N-(2,6-dimethylphenyl)-1-propyl-2-piperidinocarboxamide, in order to achiever compounds and pharmaceutical compositions presenting diverse enantiomeric excesses of (S)-N-(2,6-dimethylphenyl)-1-propyl-2-piperidinocarboxamide, in order to quantify and determine the participation of (R)-N-(2,6-dimethylphenyl)-1-propyl-2-piperidinocarboxamide in the anesthetic and cardiotoxic effects. These compounds and compositions enantiomerically manipulated demonstrate to present a significant improvement in itsanesthetic properties, presenting a cardiotoxic profile equivalent to pure enantiomer, a (S)-N-(2,6-dimethylphenyl)-1-propyl-2-piperidinocarboxamide.

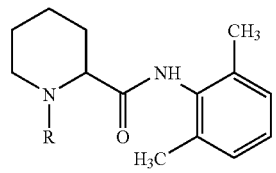

5 Claims, 3 Drawing Sheets

U.S. PATENT DOCUMENTS

| | | |
|---|---|---|
| 5,777,124 A | 7/1998 | Zavareh et al. |
| 5,786,484 A | 7/1998 | Dyer et al. |
| 5,959,112 A | 9/1999 | Jaksch |
| 5,994,548 A | 11/1999 | Langston et al. |
| 6,384,227 B2 | 5/2002 | Dyer et al. |

OTHER PUBLICATIONS

Stereoselective interaction between the R enantiomer of warfarin and cimetidine. 1986, Choonara et al.*

Importance of Drug Enantiomers in Clinical Pharmacology 1985, Drugs vol. 30, pp. 333-354. Kenneth Williams et al.*

* cited by examiner $R = H, CH_3, C_2H_5, C_3H_7, C_4H_9, C_5H_{11}$

NON-RACEMIC MIXTURES OF (S) AND (R) ENANTIOMERS OF N-(2,6-DIMETHYLPHENYL)-1-PROPYL-2-PIPERIDINOCARBOXAMIDE; RELATED PROCESSES AND PHARMACEUTICAL COMPOSITIONS

The present invention is basically related to the pharmacology field, more precisely in the anesthesiology area.

Ropivacaine corresponds to the laevorotatory enantiomer from N-2,6-dimethylphenyl)-1-propyl-2-piperidinocarboxamide, that is, a (S)-N-(2,6-dimethylphenyl)-1-propyl-2-piperidinocarboxamide.

Belonging to the series of local anesthetics homologous to bupivacaine, ropivacaine was recently introduced as pure enantiomer, contrary to its antecessors, bupivacaine and mepivacaine.

In FIG. 1 are represented the structures of the homologous anesthetics to which these substances belong to.

Studies carried out on the structure and activities of the anesthetics belonging to the series of local anesthetics homologous to bupivacaine (FIG. 1, where $R=C_4H_9$) demonstrates that when the substituent bound to the nitrogen from piperidine ring ranges from methyl to penthyl, various alterations of the properties of these anesthetics are observed. Aberg, G. describes that in as much as the number of carbon atoms bound to the nitrogen from piperidine ring of the mepivacaine molecule ($R=CH_3$) increases, forming a chain of four or five carbons, the toxicity of the compounds and the duration of its local anesthetic effects are expanded. With longer N-alkyl chains, containing more than five carbon atoms, the general toxicity and the local anesthetic power (but not the tissue toxicity) are reduced. Aberg, G., Dhunér, K-G. and Sydnes, G. "Studies on the Duration of Local Anesthesia: Structure/Activity Relationships in a Series of Homologous Local Anesthetics" Acta. Pharmacol. et Toxicol. 1997, 41: 432-443). The fact that the toxicity and the power of these chain derivatives containing more than five carbon atoms being reduced, seems to be related to the possibility of formation of dimers, polymers or micelles, being the possible reasons that these molecules of long chain to present lower toxicity and demonstrate to be less effective as local anesthetics when compared to the medium chains (Friberger, P. & G. Aberg, "Some Physiochemical Properties of the Racemates and the Optically Active Isomers of two Local Anesthetic Compounds", Acta Pharm. Suec., 1971, 8: 361-364; Johnson, E. M. & Lundlum, D. B., "Use of Trypan Blue and Rabbit Eye Tests for Irritation", J. Amer. Pharm. Ass. (Scient. Ed.) 1950, 39: 147-151; Neville, G. A. & Cook, D., "Lidocaine—An Unusual Incidence of an Acyclic cis Amide Configuration", J. Pharm. Sci., 1969, 58: 636-637.).

In addition to the differences of activities described above, this series of homologous anesthetics present another important peculiarity. The presence of a chiral carbon in its structure gives to these substances, the property of existing in the form of two distinct enantiomers for each carbon atom added in the N-alkyl chain. The enantiomers are molecules which, for containing one or more atom of chiral carbon can exist in the form of two distinct spatial structures, being one the specular image of the other and that are not susceptible of superposition, in reality consisting of structurally different molecules, despite presenting the same physical-chemical properties, except its specific rotations that are opposite.

The importance of this observation is based on the fact that the chirality is an important attribute of the majority of biological process and that the enantiomers of bioactive molecules frequently have different biological effects. The explanation for this observation falls on the fact that many drugs are specific, and the action of these drugs is usually explained on basis of the Receptors Theory. The receiving molecules in the body are proteins that show high affinity of its ligands to certain molecular structures, such affinity being analogous to the bonding of one enzyme to its substrate. The bonding of one substrate to its receptor shoots a mechanism (for example, the modification of the activity of one enzyme, transport of ions, etc., which are manifested in the form of a biological reply. Irrespective of its physiological functions, the receptors present a characteristic in common: they are chiral molecules and can be expected to be enantioselective in its bonding to these messenger molecules. (Aboul-Einen, H.; Wainer, I. W. "The Impact of Stereochemistry on Drug Development and Use" Chemical Analisys 142: 5 (1997)).

When an enantiomer shows a high grade of complementarities with the site of action (eutomer), it interferes in the action of its antipode, making it inactive (distomer). This phenomenon, Äriens E J ("Stereochemistry, a Basis for Sophisticated Nonsense in Pharmacokinetics and Clinical Pharmacology." Eur. J. Clin. Pharmacol., 26: 663-668 (1994)) named "isomeric ballast", literally "an isomeric counterbalance". It is the case of atropine, which is naturally yielded as an S-enantiomer and during the extraction process suffers racemization, resulting in the relation S/R 50:50, being the R-enantiomer absolutely inactive as anticholinergic. In clinic it is used in this racemic form.

Twenty five percent of the medicaments currently used in medicine, contain one or more chiral carbons, being 80% of these, commercialized in its racemic forms (Calvey TN—Chirality in Anesthesia. Anesthesia, 47:93-94 (1992)).

The inactive enantiomeric form (distomer), however, it is not always a passive component in the mixture, being able to act as agonist, antagonist, exercise actions in other receptors, produce undesirable side effects or also contribute to the total efficacy of the racemate (Willians K, Lee E—Importance of Drug Enantiomers in Clinical Pharmacology. Drugs, 30:333-354 (1985)).

Some examples are given hereunder, in which there are differences of activity between the enantiomers of drugs commercialized in its racemic forms: cetamine contains S-cetamine which is predominantly anesthetic and hypnotic, whilst R-cetamine is the main source of undesirable side effects (psychotic reactions when waking up); in the case of propoxyphen, o (2S,3R)-(−)-propoxyphen is anti-coughing, whilst (2R,3S)-(+)-propoxyphen is analgesic; prilocaine shows the isomers R-prilocaine being more rapidly metabolized than S-prilocaine, induces increase in the plasmatic concentration of ortho-toluidine and methahemoglobine.

The obtainment of chiral molecules through usual synthetic procedures, normally elapses forming equal quantities of both enantiomers, producing racemic substances. When the homologous series of bupivacaine was discovered, the synthetic drugs were essentially produced in its racemic forms, due to innumerous technological difficulties.

The advancements achieved in the field of Asymmetric Synthesis, the development of modern techniques in the obtainment of enantiomers through processes of racemic mixtures separation, the fall of prices in the production of resolution agents and the development of efficient techniques for analysis of these substances, today, makes the production of industrially distinct enantiomers possible, enabling the differentiated study of these new molecules.

On account of the advancements, many molecules that were developed in past decades as racemic, are again under study in the form of its distinct enantiomers. In this context ropivacaine has arisen as a pure laevorotatory enantiomer, which initial promise was to be a safer option to the use of racemic bupivacaine, anesthetic of preference in local anesthesia of long duration.

The preliminary studies comparing racemic ropivacaine and bupivacaine for epidural anesthesia in 0.5% and 0.75% concentrations found characteristics of similar sensorial blockings, despite the duration of the sensorial blocking being significantly shorter in some studies (Kerkkamp H E M, Gielen M J M, Edstrφm H. Comparison of 0.75% ropivacaine with epinephrine and 0.75% bupivacaine with epinephrine in lumbar epidural anesthesia. Reg Anesth 1990; 15:204-207; Brown D L, Carpenter R L, Thompson G E. Comparison of 0.5% ropivacaine and 0.5% bupivacaine for epidural anesthesia in patients undergoing lower extremity surgery. Anesthesiology 1990; 72:633-636), showing the tendency of a sensorial blocking significantly shorter in other studies. In brachial plexus anesthesia, ropivacaine and bupivacaine demonstrate to be equally efficient. In another study, comparing racemic ropivacaine and bupivacaine at 0.2% for pain relief, ropivacaine was associated to a motor blocking many times lower than bupivacaine (Muldoon T, Milligan K, Quinn P, Connolly D C, Nilsson K. Comparison between extradural infusion of ropivacaine or bupivacaine for the prevention of postoperative pain after total knee arthroplasty. Br. J. Anaesth. 1998; 80:680-681). Another comparative study of racemic ropivacaine and bupivacaine for spinal anesthesia, demonstrated that ropivacaine is about 50% less potent than racemic bupivacaine (Gautier PhE, De Kock M, Van Steenberge A, Poth N, Lahaye-Goffart B, Fanard L, Hody J L. Intrathecal ropivacaine for ambulatory surgery. Anesthesiology 1999; 91:1239-1245).

These studies evidenced that ropivacaine is less efficient in a series of customary procedures with the use of bupivacaine. In order to compensate the differences of activity between these anesthetics, doses relatively higher of ropivacaine have been used to achieve the local anesthetic effect adequate for long procedures. This tendency is leading the researchers to use quantities almost twice superior of this anesthetic for obtainment of effects close to that of racemic bupivacaine. However, the increase of concentrations of formulations or of its dosages shall lead, directly, to the increase of the cardiotoxic potential of these anesthetic formulations, with the consequential disappearance of the initial clinic advantage of a less cardiotoxic profile of ropivacaine when compared to bupivacaine.

Several studies carried out with ropivacaine demonstrate the necessity of doses much higher than the bupivacaine doses, seeking to obtain effects close to this anesthetic. Among them are the study carried out by Chung and collaborators, in which hyperbaric ropivacaine was compared to hyperbaric bupivacaine in cesareans, being employed a quantity effectively higher of ropivacaine in relation to bupivacaine, 18 mg and 12 mg respectively (a relation of 0.066 mol of ropivacaine for 0.042 mol of bupivacaine) and the results demonstrated that sensorial blocking and motor blocking are inferior to those obtained with racemic bupivacaine (Chung C J, Choi S R, Yeo K H, Park H S, Lee S I, Chin Y J—Hyperbaric spinal ropivacaine for cesarean delivery: a comparison to hyperbaric bupivacaine. Anesth. Analg. July; 93: 157-161 (2001)). Fernandes-Guisasola and collaborators, in a comparative study of the use of bupivacaine with fentanyl and ropivacaine with fentanyl in epidural analgesia in deliveries, used bupivacaine at 0.0625% with fentanyl, comparing ropivacaine at 0.1% with fentanyl, using quantities in volume identical among these anesthetics and obtaining equivalent results for both compositions, proving that bupivacaine is more potent than ropivacaine (Fernandez-Guisasola J, Serrano, M L, Cobo B, Munos L, Plaza A, Trigo C, Del Valle SG—A comparison of 0.0625% bupivacaine with fentanyl and 0.1% ropivacaine with fentanyl for continuous epidural labor analgesia. Anesth. Analg. May; 92(5): 1261-1265 (2001)). Another study was conducted by Junca and collaborators, comparing bupivacaine with ropivacaine for cervical plexus blocking using bupivacaine at 0.5% and ropivacaine at 0.75%. As a result, have observed that a greater dose of ropivacaine is necessary in comparison to bupivacaine (225 mg of ropivacaine to 150 mg of bupivacaine), however, with a postoperative analgesia inferior to that obtained with bupivacaine, besides greater plasmatic concentrations of ropivacaine, there existing no reason for the use of ropivacaine in these types of procedures (Junca A., Marret E., Goursot G., Mazoit X., Bonnet F.—A comparison of ropivacaine and bupivacaine for cervical plexus blocking—Anesth. Analg. March; 92(3): 720-724 (2001)).

These results demonstrate that ropivacaine shall have its use restricted to a small parcel of procedures and anesthetic techniques, in which can substitute bupivacaine in a satisfactory manner.

As previously discussed, ropivacaine is the laevorotatory enantiomer of N-(2,6-dimethylphenyl)-1-propyl-2-piperidinocarboxamide, a (S)-N-(2,6-dimethylphenyl)-1-propyl-2-piperidinocarboxamide. In its racemic form the laevorotatory and dextrorotatory enantiomers are present in equal quantities. Studies carried out with the racemic form at N-(2,6-dimethylphenyl)-1-propyl-2-piperidinocarboxamide demonstrated that it presents a sensorial and motor blocking effects, a little inferior to bupivacaine and a cardiotoxic potential close to that presented by bupivacaine.

This racemic form was not introduced in the anesthetic practice due to the best therapeutic profile observed with the use of its homologous bupivacaine. Its recent entry in the anesthetic practice in the form of a sole enantiomer, occurred due to its reduced cardiotoxic potential if compared to the racemic form of bupivacaine. The use of this pure laevorotatory form gave the effective advantage to this anesthetic on the racemic bupivacaine, however, the exclusion of its dextroenantiomer demonstrated to interfere reducing, significantly, the power achieved by this anesthetic which, on its racemic form, presents a behavior profile very close to that presented by bupivacaine.

Until lately, the studies carried out with enantiomeric substances aim at the obtainment of pure enantiomers, in order to find out which enantiomer presented a certain desired effect, usually disregarding to the other enantiomer, the distomer, the presence of the side effects observed. The fact that the distomer having more intense side effects associated or attributed thereto, lead the researchers to ignore its probable presence in the final medicament, even in cases where it demonstrates to also present the desired properties that are present in eutomer. The studies carried out therefrom, have considered only the more adequate enantiomeric form, being this the one that presents little side effects in relation to the other. Therefore, few studies are carried out with the less adequate enantiomeric forms, in many cases, leading not to understand which activity mechanisms that the racemic drugs have, that, in some cases, makes them more efficient than its pure enantiomers, despite presenting some side effects, comparatively, more pronounced.

Recently, more attention is being given to special cases where the presence of both enantiomers of substances, seem to be effectively more adequate to the activity profile of chiral drugs. Apparently, the first drug where the use of both enantiomers was promoted for the obtainment of an ideal therapeutic or pharmacological profile was the indacrinone, where both enantiomers were employed in molar quantities not equivalent among them, in order to achieve an improvement on its activity. Its laevoisomer demonstrated to be a natriuretic agent, more potent than its dextroisomer. The relatively high uricosuric/natriuretic ratio of its dextroisomer, offered the opportunity to improve the pharmacological profile of this drug. The enantiomeric manipulation of indacrinone was conducted with the objective to observe if the increase of the dextroisomer ratio, in relation to laevoisomer could prevent or revert the hiperuricemic effect of the racemate, without inducing natriurese. This study revealed that the ideal proportions between the enantiomers ranged between 60 to 77% of enantiomeric excesses of its dextroisomer (Tobert J Á, Cirillo V J, Hitzenberger G, James I, Pryor J, Cook T, Brentinx S, Holmes I B & Lutterbeck P M—Clin. Pharmacol. Ther., 29:344-350 (1981)).

Recently, other drugs have undergone this same type of study, where advantages in the use of both enantiomers to achieve a more adequate activity profile are observed. It is the case, for example, of patent WO 98/40053, where the authors promote the use of both enantiomers, mainly, of tramadol and warfarin in delivered speeds of the non-equimolar enantiomers for the obtainment of an ideal activity profile for these drugs. The enantiomers can be used or manipulated in the pharmaceutical forms, in order to present a delivered profile differentiated between them, so that one is delivered prior to the other, or more quickly than the other. The racemic tramadol presents (+)-tramadol, that despite being a more potent analgesic than the racemic form and the (−)-tramadol, presents greater incidence of side effects like nauseas or dizziness associated thereto. The more adequate therapeutic form would be the quick delivery of (−)-tramadol and of controlled delivery of (+)-tramadol, in order to reduce the side effects associated to the latter, since there is a complementary and antinoceptive synergistic effect among the tramadol enantiomers. In the case of warfarin, an anticloting, both enantiomers present a hypoprothrombinemic activity, being (S)-warfarin more potent. However, the use of this form of warfarin and even of its racemic form is complicated by the fact that a delay of some days in the establishment of the adequate anticloting effect, existing the necessity of establishing a restricted balance between the under dosing and the overdosing. This delay in the establishment of the effect seems to be associated to different activities of the warfarin enantiomers bound to albumen, being metabolized by different routes, which in its turn, shall influence in the expulsion speeds thereof.

The patent WO 00/32558, describes the use of tramadol enantiomers in quantities different from those found in racemic tramadol, where (−)-tramadol is employed in a quantity of at least 60% by weight, comparatively to (+)-tramadol, corresponding to an enantiomeric excess of 20% of (−)-tramadol. The employment of non-equimolar quantities of both enantiomers show advantages on the administration of the racemate and/or of (+)-tramadol, that the administration seems to raise not only the desired effect of this anesthetic, but also increase its side effects of nauseas and dizziness. Although being less active the (−)-tramadol seems to be bound to the modulation of the emetic properties of tramadol, reducing the global emetic capacity of the racemate.

In the literature there are several procedures describing the obtainment of ropivacaine, but none of these procedures establish a practical and economic method in its obtainment and of its dextroenantiomer, simultaneously.

The patent WO 85/00599 describes a procedure proposing the obtainment of ropivacaine in four synthetic phases, starting by the optical resolution of the racemic pipecolic acid with L-(+)-tartaric acid, the subsequent obtainment of the chloridrate of its acid chloride, its posterior condensation with 2,6-dimethyl aniline, the alkylation of its pipecoline ring with n-propyl bromide and the obtainment of its chloridrate to be employed as an active salt in the end product. The procedure described uses a resin of special ionic-exchange, very expensive for the isolation of the L-pipecolic acid, failing which it becomes impossible to continue the synthetic procedure to achieve ropivacaine. In addition to the high cost of the resin employed, another problem related to this procedure is due to the partial racemization of the L-pipecolic acid during the posterior phase, leading to a considerable reduction of the global yield in obtainment of ropivacaine. The procedure described also does not give an example of the obtainment of the dextroenantiomer of ropivacaine, which can be achieved in a form analogous to that of ropivacaine; however, upon employing the tartrate of D-pipecolic acid isolated in the first phase, in its solid form, suffering the same problems of the obtainment of ropivacaine, that is, the use of the special resin and partial racemization.

Another procedure for obtainment of ropivacaine is described in patent WO 96/36606, in a process which is composed of three synthetic phases. At an initial phase, racemic pipecolylxilydide suffers an optical resolution process through the use of L-(−)-dibenzoil tartaric acid, achieving S-pipecolylxilydide. At a second phase, S-pipecolylxilydide is alkyled with bromopropane or iodopropane and its chloridrate salt is isolated in raw form. The final phase consists in recrystallization of this chloridrate salt, in order to achieve its monohydrated salt. In this procedure racemization is not described during its performance, however, the cost of the resolution agent employed is considerably high, increasing overmuch the production cost of this enantiomer. Likewise in previous patent, this patent also does not describe the obtainment of ropivacaine dextroenantiomer, however, investigative studies with this procedure, carried out by us, demonstrated that its obtainment is problematic due to the difficulty of crystallization and purification of R-pipecolylxilydide obtained from L-dibenzoil tartaric acid.

Patent WO 96/12699 describes a procedure mentioning to be adequate for the obtainment of either ropivacaine or the laevorotatory enantiomer of bupivacaine, the levobupivacaine. Its experimental part is exclusively directed to the obtainment of levobupivacaine, existing no reference to how to effect the procedure for the other analogous, among which ropivacaine is found. In this procedure non-natural tartaric acid is employed, ((S,S)tartaric acid or D-(−)-tartaric acid) as resolution agent, using as solvent, an alcohol and water and/or less than 0.5 molar equivalent of this resolution agent. This procedure directed to the obtainment of levobupivacaine when employed in the conditions described for the obtainment of ropivacaine, shows to be inefficient, presenting very low yields due to the high solubility of the diastereomeric salt in the medium proposed. In addition to this fact, the resolution agent employed presents very high cost if compared to the natural tartaric acid, making the process of obtainment of N-(2,6-dimethylphenyl-1-propyl-2-piperidinocarboxamide enantiomers economically unfeasible.

We can verify that for the obtainment of ropivacaine and dextroropivacaine enantiomers, the procedures described so far are very expensive, industrially complex, susceptible to racemizations and to low yields and, mainly, directed only to the obtainment of ropivacaine, not describing or considering the technical difficulties existing in the obtainment of this dextroenantiomer.

For the obtainment of industrial quantities of both enantiomers of N-(2,6-dimethylphenyl)-1-propyl-2-piperidinocarboxamide, it becomes necessary that a simple procedure, in which both enantiomers can be quickly achieved from a usual advanced substrate, preferably being it the N-(2,6-dimethylphenyl)-1-propyl-2-piperidinocarboxamide itself.

Thus, one of the objectives of the present invention is to describe an unpublished process and very simple to be industrially effected for the obtainment of both enantiomers of N-(2,6-dimethylphenyl)-1-propyl-2-piperidinocarboxamide.

Previously, we have also verified that the ropivacaine currently employed in anesthetic and/or analgesic procedures demonstrated an activity much lower than that achieved by bupivacaine. This fact is leading the researchers to employ doses that can be twice over that employed for bupivacaine, without achieving the quality of the motor blocking achieved with bupivacaine.

Despite being less toxic than bupivacaine, ropivacaine does not fail to present a toxic potential, which will certainly manifest itself, due to the necessity of employment of doses excessively high to achieve effects close to those achieved with bupivacaine. Due to this profile of activity, ropivacaine has its use directed only to very specific procedures, unable to have its use expanded in order to substitute bupivacaine in a great quantity of procedures where the employment of a less toxic anesthetic would bring greater security to the patient and to the anesthesiologist.

Previously, we went through a line of more specific studies demonstrating that in some cases the use of both enantiomers of a racemic substance in quantities non-equimolar between itself, can provide advantages on the use of pure enantiomers in the formulation of pharmaceutical compositions.

We have also verified that there is no study carried out in order to observe the possible contribution of small quantities defined of dextroropivacaine in the anesthetic effect of ropivacaine.

Thus, another objective of the present invention is to provide the enantiomeric manipulation of ropivacaine, through the reduction of the enantiomeric excess in this laevoisomer, quantifying the participation of dextroenantiomer in anesthetic and cardiotoxic effects, in order to improve the anesthetic profile of ropivacaine. The compounds and compositions are manipulated enantiomerically, forming non-racemic mixtures between the enantiomers of N-(2,6-dimethylphenyl)-1-propyl-2-piperidinocarboxamide.

The ropivacaine currently employed presents an enantiomeric excess higher than 99.9% (99.95% of ropivacaine and 0.05% of dextroropivacaine), dealing with a pure enantiomer. We verified that upon promoting the reduction of the enantiomeric excess of ropivacaine, through the employment of dextroenantiomer of N-(2,6-dimethylphenyl)-1-propyl-2-piperidinocarboxamide, the compositions enantiomerically manipulated started to present an activity higher than that of pure ropivacaine, however, presenting a toxicity practically equivalent to that presented by ropivacaine. These compositions enantiomerically manipulated may be employed in a great variety of procedures where anesthetic activities higher than that presented by ropivacaine are desired, expanding considerably its use that is currently restricted to some specific procedures.

A third objective of the present invention is the use of ropivacaine in enantiomeric excesses lower than 99%, in medicine and veterinary.

BRIEF DESCRIPTION OF THE DRAWINGS

FIG. 1 is a structural diagram of the homologous anesthetics to which ropivacaine belongs to;

DESCRIPTION OF THE INVENTION

Figure 1:
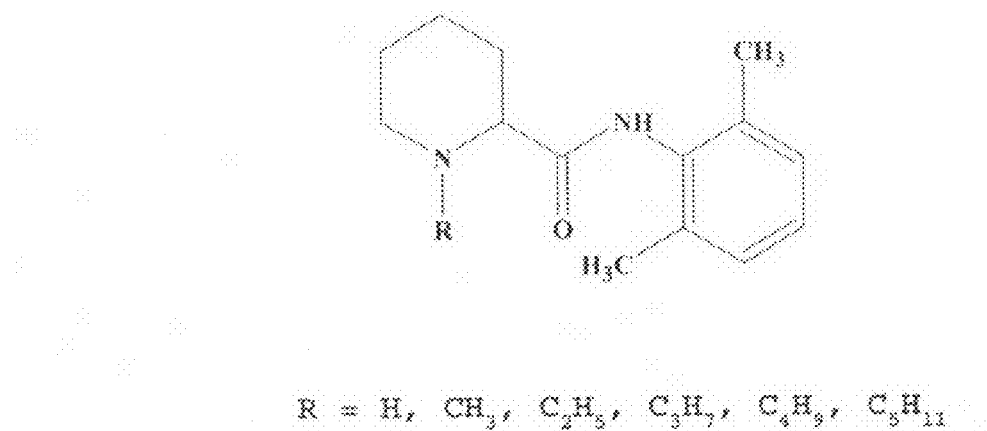

In accordance with the present invention, the process for the obtainment of enantiomers of N-(2,6-dimethylphenyl)-1-propyl-2-piperidinocarboxamide consists of the following phases:
(a) Dissolve N-(2,6-dimethylphenyl)-1-propyl-2-piperidinocarboxamide in its freebase form, in an adequate organic solvent;
(b) Add the resolution agent in quantity not lower than 0.5 molar equivalent in relation to N-(2,6-dimethylphenyl)-1-propyl-2-piperidinocarboxamide;
(c) Add water in volume not higher than 6% of the volume of the organic solvent employed in (a);
(d) Maintain the system under reflux until full dissolution of solids;
(e) Allow the system cool, add tartrate germs of (R)-N-(2,6-dimethylphenyl)-1-propyl-2-piperidinocarboxamida and leave the system under stirring until full precipitation of solids;
(f) Filter the tartrate of (R)-N-(2,6-dimethylphenyl)-1-propyl-2-piperidinocarboxamide;
(g) Add the resolution agent to the filtrate in quantity not lower than 0.5 molar equivalent in relation to the quantity of N-(2,6-dimethylphenyl)-1-propyl-2-piperidinocarboxamide primarily used;
(h) Maintain the system under reflux until full dissolution of solids;
(i) Allow the system cool, add tartrate germs of (S)-N-(2,6-dimethylphenyl)-1-propyl-2-piperidinocarboxamide and leave the system under stirring until full precipitation of solids;
(j) Filter the tartrate of (S)-N-(2,6-dimethylphenyl)-1-propyl-2-piperidinocarboxamide.

In accordance with the process described, the obtainment of enantiomers of N-(2,6-dimethylphenyl)-1-propyl-2-piperidinocarboxamide can be directly effected in a sole initial phase, which consists of employing this racemic substrate, submitting it to the resolution with L-(+)-tartaric acid (also known as (R,R)tartaric acid or natural tartaric acid), precipitating the dextroenantiomer (dextroropivacaine or (R)-ropivacaine) in the form of a solid salt, which can be easily separated from the solution, the laevoenantiomer (ropivacaine) remaining in solution.

The subsequent phase of the process consists of purification phases through recrystallizations and the transformation of the freebases into chloridrate salts, in order to achieve adequate pharmaceutical salts of these substances.

In accordance with the present invention the tartrate salts isolated present high enantiomeric excesses, being that in the obtainment of end enantiomers, ropivacaine and dextroropivacaine, in the form of its acceptable pharmaceutical salts becomes very simple.

In accordance with the present invention, N-(2,6-dimethylphenyl)-1-propyl-2-piperidinocarboxamide is dissolved in a miscible organic solvent with water, as the alcohols $C_1$-$C_6$, among which, methanol, ethanol, propanol, isopropanol, butanol, among others, ketone or tetrahydrofuran (THF), as well as in solvents, not miscible with water, as esters, among which, ethyl acetate, ketones, among which, acetone, methyl isobutylketone and ethers, among which, diethyl ether and methyl tert-butyl ether (MTBE). Among the solvents employed in the resolution process, the preferred solvents are the alcohols, ketones and ethers miscible with water, specially ethanol, isopropanol, acetone and tetrahydrofuran (THF).

The resolution agent employed is L-(+)-tartaric acid (also known as (R,R)-tartaric acid or natural tartaric acid), which is the resolution agent of lower cost existing in the market. In accordance with the procedure, the resolution agent is employed in a quantity which can range from 0.50 molar equivalent to 0.85 molar equivalent in relation to the substrate (N-(2,6-dimethylphenyl)-1-propyl-2-piperidinocarboxamide). The use of the resolution agent in a quantity lower than the molar equivalent quantity of the racemic substrate, grants to the procedure more stability to the process, yielding a product of greater enantiomeric excess than that usually achieved with the use of the molar equivalent quantities between the resolution agent and the racemic freebase. In addition to the enantiomeric excess achieved through this procedure be considerably higher, thus, prevent the possibility of concurrent crystallization of both diastereomeric salts due to quenching of the reaction medium.

In the resolution phase was observed that the employment of solvents containing a small percentage of water, grants more facility in the solubilization of the substrate and the resolution agent, granting also more stability to the reaction medium, which can be quenched at room temperature without influencing, significantly, in the purity of the diastomeric salt achieved, reducing the time of the process. In the process conditions, the percentage of water employed can range between 2% to 6% by volume, relative to the solvent employed in the resolution phase. The employment of superior quantities of water reduces, considerably, the yielding of the reaction, due to the great solubility of this tartrate in the end solution.

In this resolution process, the precipitation of (R)-N-(2,6-dimethylphenyl)-1-propyl-2-piperidinocarboxamide (dextroropivacaine or R-ropivacaine) occurs firstly in the form of tartrate salt. For the precipitation of this salt from the reaction medium, is necessary the use of tartrate germs of (R)-N-(2,6-dimethylphenyl)-1-propyl-2-piperidino-carboxamida (dextroropivacaine tartrate) to sow the medium, in order to induce its precipitation. This diastereomeric salt is separated from the reaction medium by conventional methods, such as filtration or centrifuging.

The freebase of dextroropivacaine is delivered through the dissolution of the tartrate salt in water and adding alkaline solutions such as, for example, sodium or potassium hydroxide solution, ammonium hydroxide concentrate, carbonates, etc.

The freebase can be achieved through its direct precipitation in the aqueous solution or can be achieved directly in organic solvent through the extraction of the alkaline medium containing the freebase with solvents non-miscible in water, such as toluene, ethyl-acetate, ether, MTBE, a metylisobutyl ketone, among other. This freebase presents high enantiomeric excess, which demonstrates to be between 90% and 98% in dextroropivacaine.

This freebase achieved can be submitted to a further purification, in order to promote the enantiomeric enrichment of the isomer achieved. Therefore, the freebase is recrystallized in organic solvents, preferably, the alcohols of $C_1$-$C_6$, toluene, and ethyl acetate, among others. Toluene and isopropanol are, specifically, the solvents, which results are the most satisfactory, considering the increase on the parameters of enantiomeric excess and the yield achieved in relation to the start material.

The obtainment of laevoenantiomer is made through the addition of L(+)-tartaric acid to the medium to which it is further sowed through the addition of tartrate of (S)-N-(2,6-dimethylphenyl)-1-propyl-2-piperidinocarboxamide (ropivacaine tartrate) to promote its precipitation. Alternatively, ropivacaine can be achieved through the evaporation of the solvent left over from the precipitation of the diastereomeric salt of dextroropivacaine. The solid material achieved is dissolved in an aqueous medium and the freebase of ropivacaine is achieved and purified in the same form described for the freebase of dextrobupivacaine.

The freebases achieved can be transformed into adequate pharmaceutical salts through the usual procedures described in the literature. For example, the chloridrates of dextrorotatory and laevorotatory enantiomers can be achieved through the dissolution of the freebase in appropriate organic solvents and further addition of gaseous chloridric acid or solution, so as to provide the precipitation of chloridrate salts. Alternatively, the obtainment of the chloridrate salt can be effected through the dissolution of the freebase of the desired enantiomer, in an appropriate solvent and subsequent addition of a saturated solvent with gaseous chloridric acid ($HCl_{gas}$) as, for example, ethyl ether saturated with $HCl_{gas}$. Among the appropriate solvents for the conversion of the freebase into chloridrate salt, preferably can be employed ethers, such as ethyl ether, methyl isobutyl ether (MTBE), tetrahydrofuran, aromatic solvents such as toluene, chlorinated solvents such as dichloromethane and chloroform, ketones as acetone and methyl isobutyl ketone, alcohols, such as isopropanol, propanol, methanol and ethanol, in addition to mixtures between these solvents.

The process described in the present invention demonstrates to be easy to perform and extremely more adequate than the previous procedures proposed for obtainment of both enantiomers of N-(2,6-dimethylphenyl)-1-propyl-2-piperidinocarboxamide.

Another objective of the present invention is to demonstrate the advantages of the use of both enantiomers N-(2,6-dimethylphenyl)-1-propyl-2-piperidinocarboxamide, dextroropivacaine and ropivacaine, in non-equimolar quantities among themselves, in the preparation of pharmaceutical compositions.

We have verified that the pharmaceutical compositions prepared containing enantiomeric excess lower than those presented by ropivacaine (which enantiomeric excess is higher than 99.9%), present a considerable and surprisingly improvement of the anesthetic profile activity that demonstrates to be superior either in the use of the racemic form, containing both enantiomers in equal quantities, as well as the use of the pure laevorotatory form.

As previously mentioned there are cases where the use of both enantiomers in obtainment of an ideal therapeutic or pharmacological profile is more adequate than the use of only one enantiomeric form. The present invention describes that this is the case of the enantiomers of N-(2,6-dimethylphenyl)-1-propyl-2-piperidinocarboxamide which, when employed in non-equivalent molar quantities demonstrate an activity higher than the racemic and laevorotatory form. The pharmaceutical compositions so prepared present a better anesthetic performance in terms of motor blocking quality, maintaining a cardiotoxicity equivalent to that observed with the employment of pure ropivacaine.

In order to achieve an activity profile higher than that presented by the racemic and laevorotatory forms, ropivacaine and dextroropivacaine are employed in quantities that can range from 55:45 by mass up to 95:05 by mass, respectively, that is, ranging from an enantiomeric excess of 10% to 90% in its laevoenantiomer.

The enantiomeric manipulation for obtainment of the enantiomeric excesses described above can be made through several forms known by those skilled in the art. As, for example, but not only restricted to these procedures, it can be made from pure enantiomers in its solid forms or solution, or can be made admixing N-(2,6-dimethylphenyl)-1-propyl-2-piperidinocarboxamide racemic to pure ropivacaine, in its solid forms or solution. Even the enantiomers presenting several enantiomeric excesses can be combined among themselves or with N-(2,6-dimethylphenyl)-1-propyl-2-piperidinocarboxamide racemic in quantities defined in order to achieve the different enantiomers excesses in ropivacaine.

In order to monitor the final enantiomeric excess, the liquid chromatography of high performance is used with the employment of chiral columns, able to separate the enantiomers, in order to quantify the desired enantiomeric excess.

The studies presented in the experimental part demonstrate to have ideal enantiomeric relations between the enantiomers of N-(2,6-dimethylphenyl)-1-propyl-2-piperidinocarboxamide, being it different from the relation 1:1 existing in the racemate and different from that existing in ropivacaine employed in the studies carried out so far, which were conducted with this form, practically pure (ee>99.9%). The results achieved demonstrate that the non-racemic compositions prepared with these combined active ingredients present significant advantages on the use of pure laevoenantiomer.

According to the present invention, the active ingredients containing enantiomeric excesses between 10% and 90% of ropivacaine can be employed in several pharmaceutical compositions, in the form of its freebases and/or its adequate pharmaceutical salts. The pharmaceutical compositions can be prepared in analogy to the compositions existing in the market or these active ingredients manipulated enantiomericaly can be employed in new pharmaceutical compositions, in which we seek for a more intense activity profile than that presented by the current ropivacaine.

Due to the surprising and significant improvement of the pharmacological profile of the compositions prepared with ropivacaine in enantiomeric excesses lower than those currently practiced for the ropivacaine existing in the market, these pharmaceutical compositions can be employed in concentrations and quantities equivalent to those used for bupivacaine, but presenting an activity higher than that observed with the pure laevorotatory form.

The results achieved demonstrate that the use of the compositions prepared containing ropivacaine in enantiomeric excess of 10% to 90% in medicine and veterinary will certainly achieve a great parcel of procedures in which the only product currently employed is the bupivacaine, offering to the medical professionals an alternative so efficient and safer than bupivacaine.

The experimental part described hereunder is composed of illustrating examples, but non-limiting; exemplifying the several possibilities included in the present invention.

EXAMPLE 01

Resolution of (R,S)-N-(2,6-dimethylphenyl)-1-propyl-2-piperidinocarboxamide

Obtainment of the Dextroropivacaine Tartrate.

In a reactor of 2.0 liters, 238 g (0.867 mol) of (R,S)-N-(2,6-dimethylphenyl)-1-propyl-2-piperidinocarboxamide were added in its freebase form and 1.075 ml of isopropanol. The system was taken to reflux, during which the dissolution of base propivacaine occurs. Thereafter, were added 71.57 g (0.477 mol) of L-(+)-tartaric acid and 32.3 ml of water (3% by volume in relation to the isopropanol volume). After addition of these reagents the system was maintained under reflux during thirty minutes, after which the heating was removed. Dextroropivacaine tartrate germs were added and the system was maintained under stirring for precipitation of the product. The precipitate product is vacuum filtered and washed in a portion of 67 ml of isopropanol. The product was dried in a stove, yielding 146 g of dextroropivacaine tartrate as a white crystal solid. MP=150°-154° C.; η=79.2%.

EXAMPLES 02 to 07

Influence of the Percentage of Water Present in the Resolution Phase

These experiments were conducted in order to study the influence of the quantity of water present in the resolution phase of (R,S)-N-(2,6-dimethylphenyl)-1-propyl-2-piperidinocarboxamide, the yield achieved and the enantiomeric purity of the salt achieved.

In every test, equal quantities of the resolution agent, L-(+)-tartaric acid and (R,S)-N-(2,6-dimethylphenyl)-1-propyl-2-piperidinocarboxamide base, were employed. Hereunder, the generic procedure adopted is found, followed by the table containing the quantities of water used in proportion to the solvent employed and the volume of water added in each experiment.

In a reactor of 100 ml, was added (R,S)-N-(2,6-dimethylphenyl)-1-propyl-2-piperidinocarboxamide base (8.86 g) and isopropanol (40 ml). The system was taken to reflux and 2.67 g of L-(+)-tartaric acid was added, followed by the quantity of water defined in table 1, hereunder:

TABLE 1

Quantity of water added per experiment

| Example | Proportion of water ($VH_2O/ViprOH$) (Volume/Volume) | Volume of water added (ml) |
|---|---|---|
| 2 | 1.0% | 0.4 |
| 3 | 2.0% | 0.8 |
| 4 | 3.0% | 1.2 |
| 5 | 4.0% | 1.6 |
| 6 | 5.0% | 2.0 |
| 7 | 5.75% | 2.3 |

After the addition of water, the reflux was maintained during thirty minutes and the heating was removed, maintaining the system under stirring. The reaction medium was sowed with dextroropivacaine tartrate germs and maintained under stirring for the precipitation of the product. The dextropivacaine tartrate was filtered, washed in 2.5 ml of isopropanol cooled and taken to the stove for drying. The following parameters were monitored:

Yield: Tartrate mass achieved in grammas;
Melting point of the tartrate salt;
Specific rotation of the freebase.

For obtainment of freebase, 2 g of the precipitate salt are dissolved in 20 ml of water and ammonium hydroxide concentrated is added up to pH=10. The freebase precipitate is filtered and washed in water and then dried in stove.

The results achieved from the experiments carried out are given in table 2 hereunder:

TABLE 2

Results of the experiments carried out to evaluate the influence of the quantity of water in precipitate tartrate salts.

| Example | Proportion of water (VH$_2$O/ ViprOH) | Yield | Melting point | Specific rotation of raw freebase (raw dextropivacaine) (c = 2, MeOH) |
|---|---|---|---|---|
| 2 | 1.0% | 102.1% | 100-122° C. | $[\alpha]_{25}^D = +3.4°$ |
| 3 | 2.0% | 59.4 | 98-102° C. | $[\alpha]_{25}^D = +60°$ |
| 4 | 3.0% | 50.0 | 98-102° C. | $[\alpha]_{25}^D = +80.4°$ |
| 5 | 4.0% | 41.6 | 98-102° C. | $[\alpha]_{25}^D = +82.2°$ |
| 6 | 5.0% | 38.8 | 98-102° C. | $[\alpha]_{25}^D = +80.88°$ |
| 7 | 5.75% | 31.5 | 98-102° C. | $[\alpha]_{25}^D = +81.10°$ |

From the results achieved we can conclude that the presence of water demonstrates to be important in the enantiomeric purity of the precipitate salt. The number 2 experiment evidences the precipitation concurrently with two salty diastereomers, that is, the dextropivacaine tartrate and the ropivacaine tartrate, the freebase achieved presenting specific low rotation, due to the low enantiomeric purity of the tartrate precipitated from the reaction medium.

Another evidence found is that the solubility of the tartrate salt increases considerably with the increase of the quantity of water added to the solvent.

EXAMPLE 08

Obtainment of Freebase of Raw Dextropivacaine 100 g of dextropivacaine tartrate were dissolved in 500 ml of water under stirring. To the solution achieved under strong stirring, about 30 ml of ammonium hydroxide were slowly added. During this procedure, the precipitation of dextropivacaine in freebase form occurs. The pH of the medium presented a value between 9 and 10. The precipitate solid is filtered, washed in water and taken to the stove for drying. The freebase dextropivacaine achieved yielded m=56.6 g as a white solid. MP=144-149° C., $[\alpha]_D^{25}$=+80° (c=2, MeOH), η=87.6%.

EXAMPLE 09

Obtainment of Dextropivacaine with Enantiomeric Excess>99.9%

56 g of dextropivacaine raw base were recrystallized from 200 ml of isopropanol, yielding 53.2 g (η=95%) of dextropivacaine pure base $[\alpha]_D^{25}$=+83.49° (c=2, MeOH), ee>99.9% (HPLC).

EXAMPLE 10

Obtainment of Dextropivacaine Chloridrate.

In a reactor of 2 liters are added 800 ml of tetrahydrofuran (THF) and 53.2 g of dextropivacaine-purified base (achieved in example 9). The mixture is stirred until full solubilization. Thereafter, 475 ml of ethyl ether saturated with gaseous chloridric acid (HCl$_{gas}$) were added, maintaining constant stirring. The reaction medium is maintained under stirring during 30 minutes and then vacuum filtered. The white solid achieved is dried in stove, yielding 61 g (η=100%) of dextropivacaine chloridrate. MP=262-263° C., $[\alpha]_D^{25}$=+6.24° (c=2, H$_2$O)

EXAMPLE 10

Obtainment of Ropivacaine Tartrate

To the resulting solution from example 1, after filtration of dextropivacaine tartrate with volume about 1.100 ml of isopropanol, 71.57 g of L-(+)-tartaric acid were added, and the mixture was refluxed during 30 minutes. After this period, the heating was turned-off and the reaction medium was maintained under stirring. The reaction medium was sowed with ropivacaine tartrate and maintained under stirring for full precipitation. The solid formed is vacuum filtered, washed in about 67 ml of isopropanol and taken to the stove for drying. MP=98°-102° C., m=126 g (η=68.4%).

EXAMPLE 11

Obtainment of Ropivacaine Raw Freebase

Under stirring, 126 g of ropivacaine tartrate were dissolved in 200 ml of water. To the resulting solution was added a solution of sodium hydroxide 1N, adjusting the pH of the solution around 10. During the addition of the alkaline solution, occurs the precipitation of raw base ropivacaine. The solid is filtered, washed in about 100 ml of distilled water and taken to the stove for drying. MP=142°-145° C., m=70 g (η=85.9%), $[\alpha]_D^{25}$=−74.6° (c=2, MeOH).

EXAMPLE 12

Obtainment of Pure Base Ropivacaine with Enantiomeric Excess Higher than 99.9%.

70.0 g of raw ropivacaine are recrystallized from 250 ml of isopropanol, yielding 59 g of ropivacaine as a crystal white solid (η=84.28%). MP=144°-146° C., $[\alpha]_D^{25}$=−83.3° (c=2, MeOH), ee>99.9% (HPLC).

EXAMPLE 13

Obtainment of Ropivacaine Chloridrate 59 g of purified ropivacaine are dissolved in 380 ml of tetrahydrofuran under stirring. To this solution under stirring, are added 300 ml of ethyl ether saturated with HCl$_{gas}$. The precipitate solid is filtered, washed with 100 ml of ethyl ether and taken to the stove for drying, yielding m=28 g (η=79.56%) of ropivacaine chloridrate. MP=260°-263° C., $[\alpha]_D^{25}$=−6.6° (c=2, H$_2$O).

The experiments described hereunder demonstrate the pharmacological activity of propivacaine isomers and the different compositions prepared with different enantiomeric excess in ropivacaine.

In these experiments the anesthetics used were prepared and named as described below:

S(−)Ropi=Pure ropivacaine—enantiomer laevorotatory of N-(2,6-dimethylphenyl)-1-propyl-2-piperidinocarboxamide;

R(+)Ropi=Pure dextroropivacaine—enantiomer dextrorotatory of N-(2,6-dimethylphenyl)-1-propyl-2-piperidinocarboxamide;

RS(±) Ropi=N-(2,6-dimethylphenyl)-1-propyl-2-piperidinocarboxamide racemic (50% dextrobupivacaine:50% ropivacaine);

(25R:75S)Ropi=Mixture enantiomerically manipulated containing 25% of dextroropivacaine and 75% ropivacaine—enantiomeric excess of 50% in ropivacaine.

Experiment 1

Study in Motor Nervous Conduction

Wistar male rats, weighing from 180 up to 250 g were under anesthesia with sodium pentobarbital (50 mg.kg$^1$) via i.p. After being submitted to tracheotomy and mechanically ventilated (Harvad Apparatus mod. 681), the animals were positioned on a surgical table (C. F. Palmer), on ventral decubital, and the four paws were fixed onto the surgical table. In the posterior face and near the back paw, the sciatic nerve was carefully dissected on both paws. A pair of platinum electrodes was fixed on the portion near the nerve and connected to a stimulator Grass mod.S88. Thereafter, the Achilles tendon was isolated and fixed to the isometric tension transducer (Grass FT03) by means of a metallic rod. The muscular shocks were induced by electrical stimulation of the sciatic nerve, with a voltage twice the maximal 0.6-1.0V), duration of 2 ms and frequency of 0.2 Hz The tension of the Achilles tendon was gradually increased until obtainment of maximum muscular shocks, which were registered in Grass polygraph (mod. 7). The body temperature was constant during the experiment. After stabilization of the preparation, the muscular shocks were registered in the absence (salty) and in the presence of increasing doses of LAs added in the proximity of the nerve. For each test, the anesthetic that socked the nerve was of 0.1 ml. The solutions were solved in physiologic serum at 0.9%, currently the experiment is maintained at 37° C. temperature.

Figure 2:
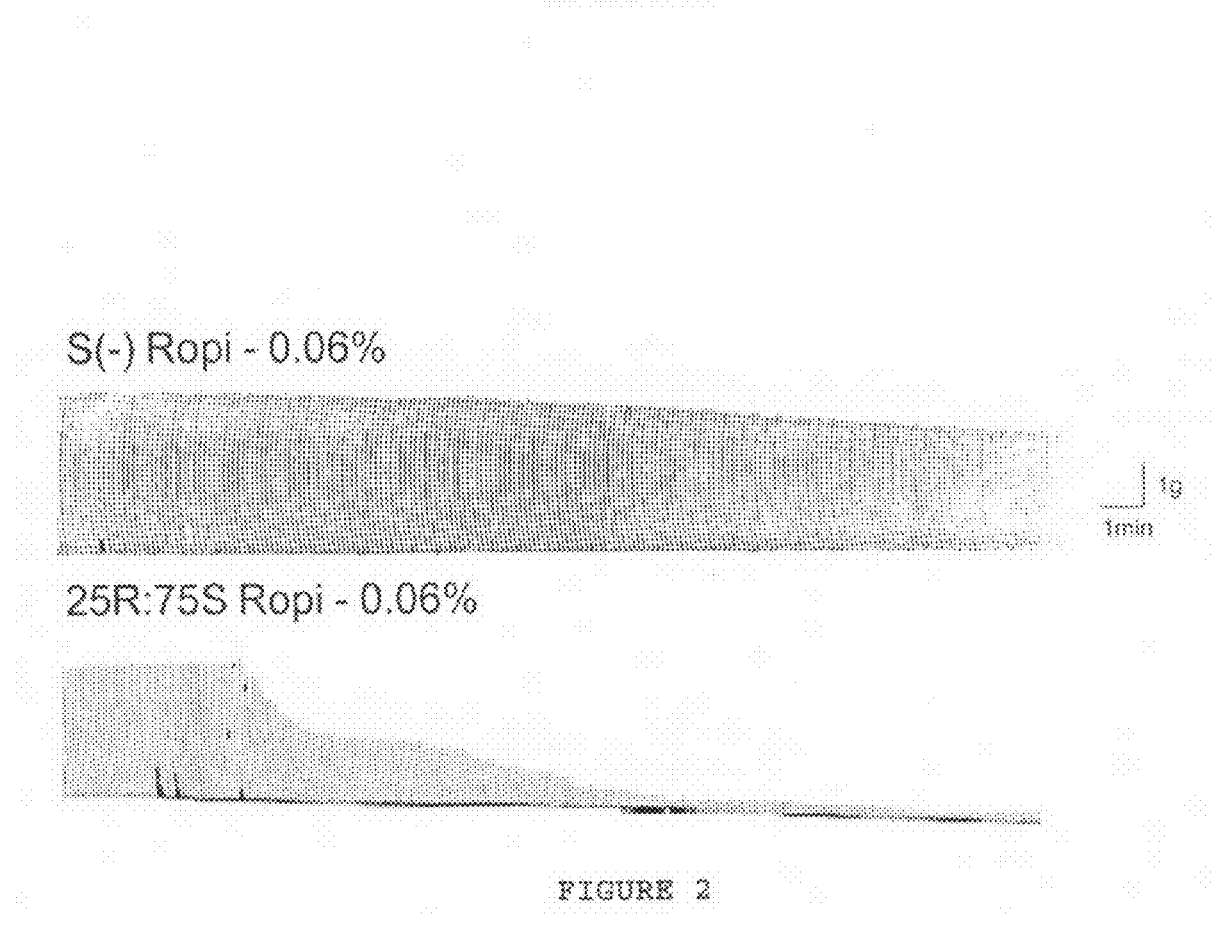
FIG. 2 is a graph showing the gastrocnemius muscle twitches of rats induced by electrical stimulation of the sciatic nerve at 0.2 Hz of frequency in the presence of the local anesthetics S(−) Ropi and 25R:75S Ropi.

Results:

FIG. 2 shows a typical experiment of motor blocking produced by the local anesthetic. Particularly, in this register, ropivacaine (S(−)ropi) and the non-racemic mixture (25R:75S) were administered in the perineural region. It should be noted the difference in the power and speed action between the anesthetic. In this figure, gastrocnemic shocks of the muscle were induced by electrical stimulation of the sciatic nerve. The segment of this nerve situated in the distal portion to the stimulation electrodes was soaked with 0.1 ml ropivacaine or with the non-racemic mixture of ropivacaine (25R:75R) in the concentration of 0.06%. The reduction of the amplitude of the muscular shocks is a function of the number of nervous motor fibers under effective action of the anesthetics.

The concentration that inhibits 50% of the amplitude of muscular shocks ($IC_{50}$) seeks is used for comparative purposes of the power between anesthetics. As showed in table 3, the power of the non-racemic and racemic mixture is approximately 80 up to 90% greater in comparison with ropivacaine, respectively.

TABLE 3

Average Inhibition Concentration ($IC_{50}$) of the Muscular Activity of the Gastrocnemic Muscle of the Rat

| Local Anesthetic | $IC_{50}$ (%) | Power relative to S (−) ropivacaine |
|---|---|---|
| S (−) Ropi | 0.070 | 1.0 |
| R (+) Ropi | 0.043* | 1.63* |
| RS (±) Ropi | 0.036* | 1.94* |
| 25R:75S Ropi | 0.038* | 1.84* |

*$p < 0.05$

Experiment 2

Effects in the Electrical Activity in Isolated Heart of the Rat (Langendorff Modified)

In the experiments "in vitro", adult male Wistar rats were used, weighing from 200 up to 350 g. The animals were slaughtered under anesthesia with ethyl ether. Thereafter, the heart was quickly removed and immersed, at room temperature, on Tyrode solution, composed in mM: NaCl, 120; KCl, 5.4; $MgCl_2$, 1.2; $CaCl_2$, 1.25; $NaH_2PO_4$, 2.0; $NaHCO_3$, 27; Glucose, 11. The pH of this solution was adjusted to 7.4±0.02, under bubbling with carbogenic mixture (95% of $O_2$ and 5% of $CO_2$).

The heart was fixed, through the aorta, to a metallic tube and the latter was connected to a peristaltic pump (Milan$^R$). In order to maintain the feasibility of the preparation, the heart was perfused with a Tyrode solution at a flow of 8 ml.min$^{-1}$ maintained at 37° C. The drugs tested were diluted in the perfusion solution in the desired concentration. Thereafter, the heart was immersed in a recipient containing 150 ml of Tyrode solution maintained at 37° C. For registration of the ECG, three pipettes (electrodes), filled in with KCl 1M were positioned inside the chamber, the nearest possible to the heart. The electrical signals generated by the heart were amplified (Amplifier type 3A9) and registered in polygraph (Gould Brush mod.2400). After stabilization of the preparation, the experimental protocol with the infusion of ALs in crescent concentrations (0.1 a 10 μM), at intervals of 5 minutes between them, was started. The heart was perfused during 5 minutes for each concentration. Only one drug was tested for each heart.

The ECG was continuously registered in the absence (control) and in the presence of drugs for analysis. After the infusion of the last concentration, the preparation was washed during 30 minutes with the Tyrode solution without the AL, aiming to evaluate the reversibility of the effect of the drug.

Figure 3:
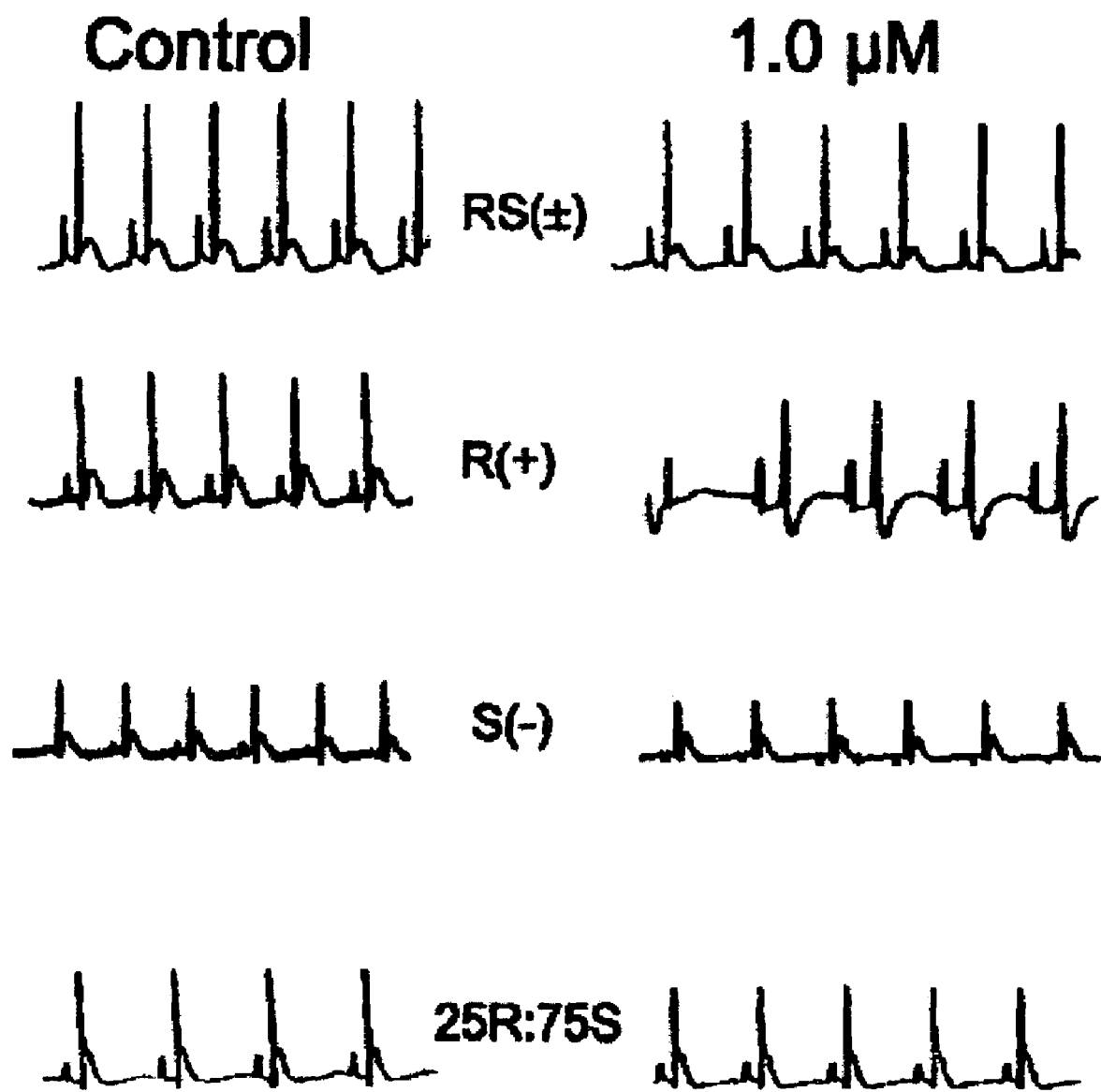
FIG. 3 is an EEG registers of isolated heart of rats in the absence (control) and in the presence of 1.0 µM of the tested local anesthetics.

Results:

The EEG registry of 4 isolated hearts is shown in FIG. 3. It is important to note that the perfusion with 1 μM of dextroropivacaine caused an important blocking of the cardiac vessel. Minimum alterations of ECG were observed with the other anesthetic in this concentration.

Figure 4:
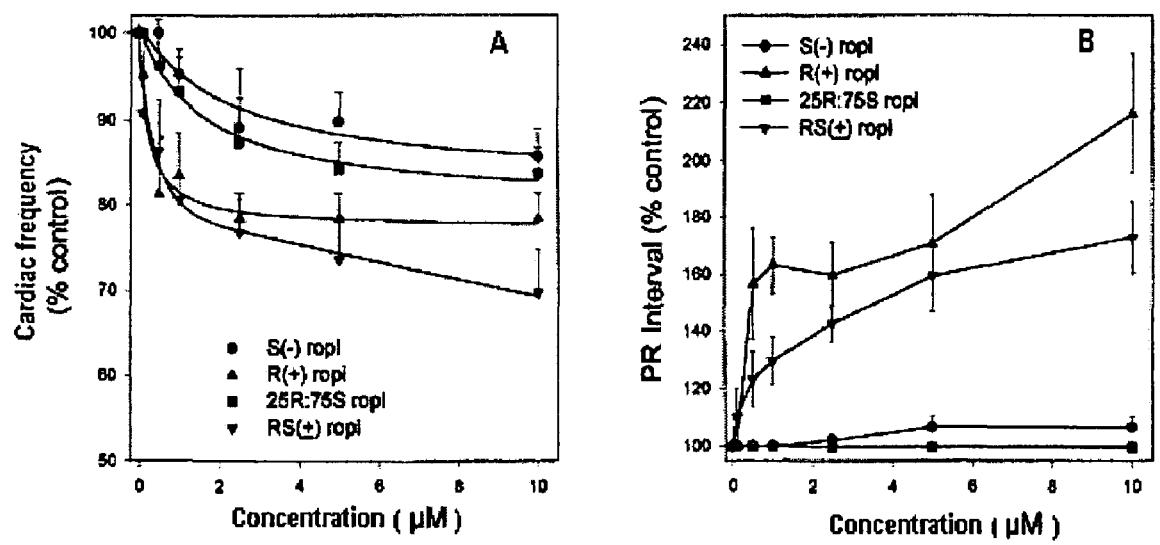
FIG. 4(A) is a graph showing the effect of the tested local anesthetics in the cardiac frequency expressed in % of control. Each point represents a mean±SEM of 6 experiments. (B) Effect of the tested local anesthetics in the PR interval of the isolated heart of a rat expressed in % of control. Each point represents a mean SEM of 6 experiments.

In FIG. 4, are presented the effects of S(−)ropi, R(+)ropi, RS(+)ropi and of (25R:75S)ropi in CF and in the PR interval of the isolated heart of a rat, versus the concentration. The points represent an average±SEM of 6 experiments.

It is evidenced that dextroropivacaine and the racemic form are those that cause greater depressors effect of CF and an increase in PR interval. This result demonstrates that the potentiality to cause arrhythmias by alterations of the cardiac conductibility is higher with these substances. Ropivacaine and the mixture (25R:75S)ropi do not alter the PR interval PR even in the concentration of 10 μM.

CONCLUSION: From the experiments described above we can conclude that the blocking power of the motor fiber is less pronounced with the use of ropivacaine enantiomericaly pure. Whereas, the mixture 25R:75S, composed of 25% of dextrobupivacaine and 75% of ropivacaine is 80% more potent in blocking motor than the pure ropivacaine.

Another conclusion relates to the cardiac toxicity, which in the mixture 25R:75S demonstrated to be comparable to that presented by ropivacaine. Either dextroropivacaine or the racemic mixture presented significantly higher cardiotoxicity in relation to ropivacaine These results confirm that the presence of dextroenantiomer in small quantities defined in ropivacaine, contributes effectively in the quality of the motor blocking achieved with pure ropivacaine without expanding, significantly, its cardiotoxic effect. The employment of ropivacaine enantiomeric excesses lower than 99% is a more efficient and safe alternative that the use of quantities and/or high concentrations of pure ropivacaine.

We claim:

1. A non-racemic mixture of (S) and (R) enantiomers of N-(2,6-dimethylphenyl)-1-propyl-2-piperidinecarboxamide, or their pharmaceutical acceptable salts, wherein the weight ratio between the (S)-enantiomer and the (R)-enantiomer is 75%:25%.

2. A process for preparing the non-racemic mixture according to claim 1 wherein said process comprising the manipulation of the enantiomeric excess by:
   (a) combining both (S) and (R) pure enantiomers of N-(2,6-dimethylphenyl)-1-propyl-2-piperidinecarboxamide, or
   (b) mixing racemic N-(2,6-dimethylphenyl)-1-propyl-2-piperidinecarboxamide with pure (S)-N-(2,6-dimethylphenyl)-1-propyl-2-piperidinecarboxamide, or
   (c) mixing enantiomeric enriched (S)-N-(2,6-dimethylphenyl)-1-propyl-2-piperidinecarboxamide with pure (R) or pure (S) or racemic N-(2,6-dimethylphenyl)-1-propyl-2-piperidinecarboxamide.

3. A pharmaceutical composition comprising the non-racemic mixture of claim 1 and a pharmaceutically acceptable carrier.

4. The composition according to claim 3 that is formulated for injection comprising an aqueous solution containing a sufficient amount of a water soluble salt of the non-racemic mixture to induce local anesthesia in a person in need thereof.

5. A method for inducing local or regional anesthesia in a human in need of being anesthetized comprising the step of administering to the human an anesthetizing amount of the composition of claim 3.

* * * * *